US008815219B2

(12) United States Patent
Carnali et al.

(10) Patent No.: US 8,815,219 B2
(45) Date of Patent: Aug. 26, 2014

(54) SUNLESS TANNING WITH PYRANONES AND FURANONES

(75) Inventors: Joseph Oreste Carnali, Trumbull, CT (US); Weimin Peng, Shanghai (CN); Xiaoxia Yang, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 22 days.

(21) Appl. No.: 13/516,818

(22) PCT Filed: Dec. 24, 2009

(86) PCT No.: PCT/CN2009/001544
§ 371 (c)(1),
(2), (4) Date: Jun. 18, 2012

(87) PCT Pub. No.: WO2011/075871
PCT Pub. Date: Jun. 30, 2011

(65) Prior Publication Data
US 2012/0251469 A1   Oct. 4, 2012

(51) Int. Cl.
*A61Q 17/04* (2006.01)
*A61K 8/35* (2006.01)
*A61Q 19/04* (2006.01)
*A61K 8/49* (2006.01)

(52) U.S. Cl.
CPC . *A61Q 19/04* (2013.01); *A61K 8/35* (2013.01); *A61K 8/498* (2013.01)
USPC ........................................................ 424/59

(58) Field of Classification Search
None
See application file for complete search history.

(56) References Cited

U.S. PATENT DOCUMENTS

| | | | |
|---|---|---|---|
| 5,232,688 A | 8/1993 | Ziegler et al. | |
| 5,523,075 A | 6/1996 | Fuerst et al. | |
| 5,612,044 A | 3/1997 | Suares et al. | |
| 5,700,452 A | 12/1997 | Deckner et al. | |
| 5,750,092 A | 5/1998 | Meyer et al. | |
| 6,033,648 A | 3/2000 | Candau | |
| 6,060,041 A | 5/2000 | Candau et al. | |
| 6,231,837 B1 * | 5/2001 | Stroud et al. | 424/59 |
| 6,313,181 B1 | 11/2001 | Cohen | |
| 6,326,033 B1 | 12/2001 | Darmenton et al. | |
| 6,399,046 B1 | 6/2002 | Schonrock et al. | |
| 6,858,216 B2 * | 2/2005 | Schulze zur Wiesche et al. | 424/401 |
| 2003/0044365 A1 | 3/2003 | Candau | |
| 2003/0082119 A1 | 5/2003 | Golz-Berner et al. | |
| 2004/0047819 A1 | 3/2004 | Hansenne et al. | |
| 2004/0086474 A1 | 5/2004 | Rabe et al. | |
| 2005/0191326 A1 | 9/2005 | Mleker | |
| 2005/0238595 A1 | 10/2005 | Stella | |
| 2006/0079417 A1 | 4/2006 | Wagner et al. | |
| 2007/0067924 A1 | 3/2007 | Beck et al. | |
| 2007/0292373 A1 | 12/2007 | Russ et al. | |
| 2008/0008668 A1 * | 1/2008 | Harichian et al. | 424/59 |
| 2008/0081057 A1 | 4/2008 | Chevalier | |
| 2008/0279796 A1 | 11/2008 | Handrosch et al. | |
| 2008/0311058 A1 | 12/2008 | Lou et al. | |
| 2009/0041688 A1 | 2/2009 | Dueva-Koganov et al. | |
| 2009/0155322 A1 | 6/2009 | Harichian et al. | |
| 2009/0247445 A1 | 10/2009 | Lou et al. | |

FOREIGN PATENT DOCUMENTS

| | | |
|---|---|---|
| EP | 0302147 A1 | 2/1989 |
| JP | 57137394 A * | 8/1982 |
| JP | 04036217 | 6/1992 |
| KR | 701222 B1 * | 3/2007 |
| WO | WO9403148 | 2/1994 |
| WO | WO9415580 | 7/1994 |
| WO | WO9421221 | 9/1994 |
| WO | WO9955303 | 11/1999 |
| WO | WO2005004833 A1 | 1/2005 |
| WO | WO2005025505 A2 | 3/2005 |
| WO | WO2011075871 A1 | 6/2011 |

OTHER PUBLICATIONS

CAPlus Abstract for KR 70122 B1, original document published Mar. 29, 2007.*
Machine translation of KR 701222, original document published Mar. 29, 2007.*
Derwent Abstract for JP 57137394 A, original document published Aug. 1982.*
CAPlus Abstract for JP 57137394 A, original document published Aug. 1982.*
PCT International Search Repor on Application No. PCT/CN2009001544, dated Dec. 24, 2009.
Written Opinion on Application No. PCT/CN2009001544, dated Dec. 24, 2009.

* cited by examiner

*Primary Examiner* — Nissa Westerberg
(74) *Attorney, Agent, or Firm* — Edward A. Squillante, Jr.

(57) ABSTRACT

A composition and method for imparting a sunless tan to skin is described. The composition and method make use of a sunless tanning agent like dihydroxyacetone in combination with an adjuvant which is a pyranone, furanone or a mixture thereof.

9 Claims, No Drawings

SUNLESS TANNING WITH PYRANONES AND FURANONES

FIELD OF THE INVENTION

The present invention is directed to a composition and method for imparting a sunless tan to skin. More particularly, the invention is directed to a composition and method that employ a sunless tanning agent as well as an adjuvant for the sunless tanning agent. The composition employs a pyranone furanone, derivative thereof or mixtures thereof as an adjuvant and, when applied, unexpectedly results in the consumer having skin with a brownish/tan coloration within a consumer acceptable time. Surprisingly, the composition does not result in color body generation even when the sunless tanning agent and adjuvant are stored together in a monophase.

BACKGROUND OF THE INVENTION

Sunless tanning agents are formulated into two types of cosmetic products. Of these, the most traditional is the self-tanning lotion. The imparted benefit is to achieve a skin coloration equivalent to that from basking in the sun. More recently, a second product category has arrived. Therein a sunless tanning agent in small amounts is added to a typical moisturizing lotion. A "glow or shine" is thereby imparted. Glow or shine is a major factor in the appearance of healthy looking skin.

Most prominent among the sunless tanning agents is dihydroxyacetone ("DHA" which is also chemically known as 1,3-dihydroxy-2-propanone). DHA, after application, is believed to exert its effect through interactions between its hydroxyl groups and the amino groups of amino acids and peptides naturally occurring in the hydrolipid pellicle and first layers of the stratum corneum of the skin. These so-called Maillard reactions are believed (see, e.g., Bobin et al., J. Soc. Cosmet. Chem. 35: 255 (1984)) to lead to formation of brown pigments in the skin, thereby giving it an appearance similar to that of a naturally obtained tan.

Unfortunately, many sunless tanning products available on the market are not stable in that they turn a yellow and/or orange color after application, especially when exposed to UV light. Other sunless tanning products perform poorly and do not quickly impart a noticeable brown color after application. Such poorly performing products do not prevent "tan-happy" consumers from basking in the sun. Products that underperform, therefore, do not protect consumers from the sun's ultraviolet rays.

There is increasing interest to develop compositions and methods for imparting a sunless tan, and especially, compositions that are storage stable. This invention, therefore, is directed to a composition and method that employ a sunless tanning agent as well as an adjuvant for the sunless tanning agent. The composition employs a pyranone, furanone and/or a derivative thereof as an adjuvant and, when applied, unexpectedly results in the consumer having skin with a brownish/tan coloration within a consumer acceptable time. Surprisingly, such a composition does not result in color body generation even when the sunless tanning agent and adjuvant are stored together in a monophase.

Additional Information

Efforts have been disclosed for making self-tanning cosmetic compositions. In U.S. Pat. Nos. 5,232,688 and 5,612,044, self-tanner compositions with DHA are described.

Other efforts have been disclosed for making self-tanning compositions. In U.S. Pat. No. 5,750,092, compositions with DHA and secondary amines are described.

Still other efforts have been disclosed for making self-tanning compositions. In U.S. Pat. No. 6,231,837, self tanning formulations comprising DHA, polyethoxyglycol and a polyol are described.

None of the additional information describes a method and/or composition that yield excellent sunless tanning results whereby the composition and method employ a sunless tanning agent and a pyranone, furanone, derivative thereof or mixture as an adjuvant.

SUMMARY OF THE INVENTION

In a first aspect, the present invention is directed to a composition comprising:
 a) a sunless tanning agent; and
 b) an adjuvant for the sunless tanning agent, the adjuvant comprising a pyranone, furanone, derivative thereof or mixture thereof.

In a second aspect, the present invention is directed to a method for generating a sunless tan comprising the step of applying to the skin the composition of the first aspect of this invention.

All other aspects of the present invention will more readily become apparent upon considering the detailed description and examples which follow.

Sunless tanning, as used herein, means obtaining the suntan look by applying a topical composition. The same can be interchanged with self-tanning. Composition, as used herein, is meant to include a substance applied to a human body for imparting a sunless tan where the composition is for example, a leave-on skin lotion, cream or mouse, shampoo, hair conditioner, shower gel, toilet bar, body wash, shaving cream, body wax, depilatory, mascara, sunscreen product or the like. Such a composition may also be put on body towelettes for application to the body. In a preferred embodiment, the composition of this invention is a lotion or cream. Consumer acceptable time means within about 3 to about 6 hours from application, and preferably, from about 1 to about 2 hours, and most preferably, from about 15 to about 30 minutes subsequent to application. A composition not resulting in color body generation means being storage stable where storage stable is defined to mean having no color bodies after about one (1) month of storage at room temperature and when formulated as a monophase product at a pH in a range from 3 to 6. Derivative thereof means derivative of a pyranone and/or furanone, and mixture thereof means any combination of a pyranone, furanone, a derivative of pyranone and a derivative of furanone.

Comprising, as used herein, is meant to include consisting essentially of and consisting of: All ranges identified herein are meant to include all ranges subsumed therein if, for example, reference to the same is not explicitly made.

DETAILED DESCRIPTION OF THE INVENTION

The sunless tanning agent suitable for use in this invention is only limited to the extent that it may be applied topically on humans to form pigmented components. Such materials may be alpha-hydroxyaldelydes and ketones, glyceraldehyde, troxerutin and related alcohol aldehydes, various indoles, imidazoles and derivatives thereof.

Illustrative yet non-limiting examples of the sunless tanning agents that may be used in this invention include dihydroxyacetone, melanin, mahakanni (eclipta alba), methyl glyoxal, erythrulose, alloxan, 2,3-dihydroxysuccindialdehyde, mixtures thereof, or the like. In a preferred embodiment, the sunless tanning agent used is dihydroxyacetone, erythrulose or a mixture thereof. In a most preferred embodiment, the sunless tanning agent is dihydroxyacetone.

Typically, the sunless tanning agent makes up from about 0.025 to about 35%, and preferably, from about 0.05 to about 15%, and most preferably, from about 0.5 to about 10% by weight of the composition, based on total weight of the composition and including all ranges subsumed therein.

The adjuvant (i.e., pyranone, furanone and/or derivatives thereof) that may be used in this invention is limited only to the extent that the same may be used in a composition suitable for topical application to humans.

Typically, the adjuvant is represented by the formulae:

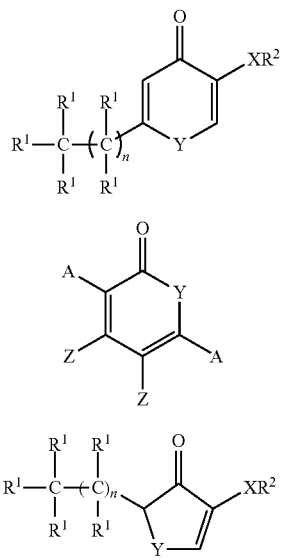

where each $R^1$ is independently H, Cl, OH, or

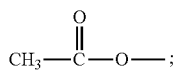

each A is independently $R^2X$— or H with the proviso that one A is $R^2X$—;
each $R^2$ is independently H, or $C_{1-4}$ alkyl;
each X is independently $NR^2$, O, S or

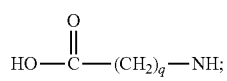

each Y is independently O, NH, $C_1$-$C_6$ alkyl substituted N or S; and
each Z is independently

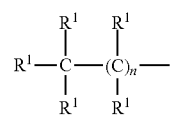

or H with the proviso that one Z is H; and
n is an integer from zero to 6, and q is an integer form 1 to 3.

In a most preferred embodiment, the sunless tanning adjuvant used in this invention is 3-hydroxy-6-methyl, 4-pyrone, often known commonly as Allomaltol. Typically, the adjuvant makes up from about 0.025 to about 35%, and preferably, from about 0.05 to about 15%, and most preferably, from about 0.5 to about 8% by weight of the composition, including all ranges subsumed therein. It is also within the scope of this invention to employ mixtures of adjuvant represented by formulae I and II. Such adjuvants may be obtained from fungi like *Aspergillus oryzae* or by art recognized techniques including those which are initiated with a Kojic acid precursor. An illustrative example of the Synthesis of Allomaltol, for example, is described in Japanese patent 4036217.

Compositions of the present invention will typically include a cosmetically acceptable carrier. Water is the most preferred carrier. Amounts of water may range from about 1 to about 99%, and preferably, from about 5 to about 90%, and most preferably, from about 35 to about 80% and optimally from about 40 to about 75% by weight, based on total weight of the composition and including all ranges subsumed therein. Ordinarily the compositions will be water and oil emulsions, most preferably, of the oil-in-water variety. Water-in-oil emulsions, and especially, those generally classified as water-in-oil and high internal phase emulsions are, however, an option. Illustrative examples of the high internal phase emulsions suitable to carry the actives and adjuvants of this invention described in commonly owned U.S. Patent Application Publication Nos. 2008/0311058 and 2009/0247445, the disclosures of which are incorporated herein by reference.

Other cosmetically acceptable carriers may include mineral oils, silicone oils, synthetic or natural esters, fatty acids and alcohols. Amounts of these materials may range from about 0.1 to about 50%, and preferably, from about 0.1 to about 30%, and most preferably, from about 1 to about 20% by weight of the composition, including all ranges subsumed therein.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, and preferably, from about 4 to about 5 silicon atoms.

Linear volatile silicone materials generally have viscosities less than about 5 centistokes at 25° C. while cyclic materials typically have viscosities of less than about 10 centistokes.

Nonvolatile silicone oils useful as carrier material include polyalkyl siloxanes, polyalkylaryl siloxanes and polyether siloxane copolymers. The essentially non-volatile polyalkyl siloxanes useful herein include, for example, polydimethylsiloxanes (like dimethicone) with viscosities of from about 5 to about 100,000 centistokes at 25° C.

An often preferred silicone source is a cyclopentasiloxane and dimethiconol solution.

Among suitable esters are:
(1) Alkenyl or alkyl esters of fatty acids having 10 to 20 carbon atoms like isopropyl palmitate, isopropyl isostearate, isononyl isonanonoate, oleyl myristate, oleyl stearate, and oleyl oleate;
(2) Ether-esters such as fatty acid esters of ethoxylated fatty alcohols;
(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxy-ethylene sorbitan fatty acid esters;

(4) Wax esters such as beeswax, spermaceti, myristyl myristate, stearyl stearate; and (5) Sterol esters, of which soya sterol and cholesterol fatty acid esters are examples thereof.

Fatty acids having from 10 to 30 carbon atoms may be included in the compositions of this invention. Illustrative of this category are pelargonic, lauric, myristic, palmitic, stearic, isostearic, hydroxystearic, oleic, linoleic, ricinoleic, arachidic, behenic and erucic acids.

Emulsifiers may be present in the compositions of the present invention. Total concentration of the emulsifier may range from about 0.1 to about 40%, and preferably, from about 1 to about 20%, and most preferably, from about 1 to about 5% by weight of the composition, including all ranges subsumed therein. The emulsifier may be selected from the group consisting of anionic, nonionic, cationic and amphoteric actives. Particularly preferred nonionic actives are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkylethercarboxylates and combinations thereof.

Cationic emulsifiers that may be used include, for example, palmitamidopropyltrimonium chloride, distearyldimonium chloride and mixtures thereof. Useful amphoteric emulsifiers include cocoamidopropyl betaine, $C_{12}$-$C_{20}$ trialkyl betaines, sodium lauroamphoacetate, and sodium laurodiamphoacetate or a mixture thereof.

Other generally preferred emulsifiers include glyceryl stearate, glycol stearate, stearamide AMP, PEG-100 stearate, cetyl alcohol as well as emulsifying/thickening additives like hydroxyethylacrylate/sodium acryloyldimethyl taurates copolymer/squalane and mixtures thereof.

Preservatives can desirably be incorporated into the compositions comprising the sunless tanning agent and adjuvant of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition, including all ranges subsumed therein.

Thickening agents may be included in compositions of the present invention. Particularly useful are the polysaccharides. Examples include starches, natural/synthetic gums and cellulosics. Representative of the starches are chemically modified starches such as sodium hydroxypropyl starch phosphate and aluminum starch octenylsuccinate. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes crosslinked polyacrylates such as the Carbomers, polyacrylamides such as Sepigel® 305 and taurate copolymers such as Simulgel EG® and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer.

Amounts of the thickener may range from about 0.001 to about 5%, and preferably, from about 0.1 to about 2%, and most preferably, from about 0.2 to about 0.5% by weight of the composition including all ranges subsumed therein.

Fragrances, fixatives and abrasives may optionally be included in compositions of the present invention. Each of these substances may range from about 0.05 to about 5%, preferably between 0.1 and 3% by weight.

To enhance skin moisturization, cationic ammonium compounds may optionally be used in the compositions of this invention. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from about 0.01 to about 30%, and preferably, from about 0.1 to about 15% by weight of the composition.

When cationic ammonium compounds are used, preferred additives for use with the same are moisturizing agents such as substituted ureas like hydroxymethyl urea, hydroxyethyl urea, hydroxypropyl urea; bis(hydroxymethyl)urea; bis(hydroxyethyl)urea; bis(hydroxypropyl)urea; N,N'-dihydroxymethyl urea; N,N'-di-hydroxyethyl urea; N,N'-dihydroxypropyl urea; N,N,N'-tri-hydroxyethyl urea; tetra (hydroxymethyl)urea; tetra(hydroxyethyl)urea; tetra (hydroxypropyl)urea; N-methyl-N'-hydroxyethyl urea; N-ethyl-N,N-N'-hydroxyethyl urea; N-hydroxypropyl-N'-hydroxyethyl urea and N,N'-dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-1-propyl or 2-hydroxy-1-propyl radicals. Most preferred is hydroxyethyl urea. The latter is available as a 50% aqueous liquid from the National Starch & Chemical Division of ICI under the trademark Hydrovance.

Amounts of substituted urea, when used, in the composition of this invention range from about 0.01 to about 20%, and preferably, from about 0.5 to about 15%, and most preferably; from about 2 to about 10% based on total weight of the composition and including all ranges subsumed therein.

When cationic ammonium compound and substituted urea are used, in a most especially preferred embodiment at least from about 0.01 to about 25%, and preferably, from about 0.2 to about 20%, and most preferably, from about 1 to about 15% humectant, like glycerine, is used, based on total weight of the composition and including all ranges subsumed therein.

Conventional humectants may be employed in the present invention. These are generally polyhydric alcohol-type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.5 to 50%, preferably between 1 and 15% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the end use composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the end use composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, willow bark, sage, thyme and rosemary.

Also optionally suitable for use include materials like lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Conventional buffers/pH modifiers may be used. These include commonly employed additives like sodium hydroxide, hydrochloric acid, citric acid and citrate/citric acid buffers. In an especially preferred embodiment, the pH of the composition of this invention is from about 3 to about 4.75, and preferably, from about 3.25 to about 4, and most preferably, from about 3.25 to about 3.75, including all ranges subsumed therein.

Colorants, opacifiers, chelators (like tetrasodium EDTA) and abrasives may also be included in the compositions of the present invention. Each of these substances may range from about 0.05 to about 5%, preferably between 0.1 and 3% by weight of the composition.

In an especially preferred embodiment, the composition of the present invention comprises less than about 5%, and preferably, from 0.01 to 4% glycine, and most preferably, no glycine.

A wide variety of packaging can be employed to store and deliver the compositions. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film.

Optionally, the composition of this invention may be divided so that a first portion may carry sunless tanning agent and a second portion may carry adjuvant. When dividing the composition, each portion should be packaged separately from each other and not come into contact with each other until application to the body. The packaging for dual compositions is known and commercially available. Upon application, the make up of the composition (i.e., the combined portions) is as described herein.

When making the composition of the present invention, ingredients may be combined in no particular order. Typically the ingredients are combined and mixed under conditions of moderate shear and at ambient temperature with pressure being atmospheric conditions. In a most preferred embodiment, DHA and adjuvant are not added at a time when mixing and heating are desired. When applied by the consumer, typically from about 1 to 5 mg, and preferably, from about 1 to 4 mg, and preferably, from about 1.5 to 2.5 mg per square centimeter of composition is applied to body surface (like skin) and including all ranges subsumed therein.

The following examples are provided to facilitate an understanding of the present invention. The examples are not intended to limit the scope of the claims.

Example 1

Illustrative adjuvant suitable for use in this invention was made in the following way:

Kojic acid (2.6 g) was dissolved in distilled thionylchloride (10 mL). The resulting mixture was stirred for about one hour at room temperature. The formed yellow crystalline mass was filtered and washed with petroleum ether and water sequentially to yield a chlorinated Kojic acid derivative. Such derivative (1.6 g) was added to 5 mL of distilled water and the resulting mixture was heated to 50° C. with stirring. Zinc dust (1.3 g) was added and followed by the addition of concentrated hydrochloric acid (3 mL) with vigorous stirring. The resulting reaction mixture was stirred for an additional three (3) hours at 70° C. Excess zinc was removed by hot filtration and the filtrate was extracted with dichloromethane.

Resulting extract was dried over anhydrous sodium sulphate, filtered and concentrated in vacuum to yield product which was purified via column chromatography or by isopropanol recrystallization.

The desired adjuvant, Allomaltol, was obtained.

Example 2

Illustrative adjuvant suitable for use in this invention was made in the following way:

Allomaltol (126 mg) and 4 mL of toluene were combined with glycine methyl ester hydrochloride (138 mg) and toluene-4-sulfonic acid monohydrate. The reaction mixture was stirred under reflux for a few days and concentrated in vacuo whereby the resulting residue was chromatographed on a silica gel column with petroleum/ethyl acetate. The resulting Kojic acid/Allomaltol derivative (20 mg) was mixed in a solvent of methanol/water (2 mL, 3:1) and 5 mg of potassium hydroxide was added. The resulting reaction system was stirred at room temperature for one (1) hour Hydrochloric acid solution (2N. 100 microliters) was added to adjust pH to circa 4. The mixture produced was dried over anhydrous magnesium sulfate and filtered to recover the desired adjuvant. Allomaltol derivative with $NHCH_2COOH$ in lieu of OH.

Example 3

Compositions comprising Allomaltol were made by mixing the following:

| Sample* | DHA (wt. %) | Glycine** (wt. %) | Allomatol (wt. %) |
| --- | --- | --- | --- |
| 1 (Control) | 5 | 5 | — |
| 2 | 5 | 5 | 0.5 |
| 3 | 5 | 5 | 1 |
| 4 | 5 | 5 | 2 |
| 5 | 5 | 5 | 3*** |

*= compositions having a balance of water
**= glycine was provided to mimic amino acid condition of skin.
***= circa 95% Allomatol was dissolved.

Visual observations and photographs of the above Samples revealed that tanning rate (color formation) was enhanced when Allomaltol was added and the rate was related to the dosage of Allomaltol employed.

Color development for the above was also assessed using a spectrophotometer set at a wavelength of 400 nm. The results from such assessment indicated that the color development at 3% Allomaltol was 20% greater than at 2%, 40% greater than at 1% and 45% greater than at 0.5% Allomaltol after 20 hours of mixing. The results also indicated that color development was 60% greater when a composition with 3% Allomaltol was compared to a composition deplete of adjuvant (with all results obtained after 20 hours of mixing the compositions).

Example 4

Compositions as described below were thoroughly mixed and stored for about 10 hours at 35° C. and 55° C.
Sample 1: DHA (5 wt. %) and glycine (5 wt. %) in 0.1 M citric acid buffer (pH=5.5)
Sample 2: Allomaltol (5 wt. %) and glycine (5 wt. %) in 0.1 M citric acid buffer (pH=5.5)
Sample 3: Allomaltol (5 wt. %) and dihydroxyacetone (5 wt. %) in 0.1 M citric acid buffer (pH=5.5)

Visual observations and photographs revealed that only Sample 1 developed a color change within the first 10 hours at both temperatures. The other two samples did not exhibit obvious color changes during the period. The results indicate that Allomaltol and dihydroxyacetone, unexpectedly, did not produce visual coloration (i.e., color bodies) during storage, thus meaning that adjuvant according to this invention may be formulated with dihydroxyacetone in a monophase product.

Example 5

Color development of the Samples of Example 3 was also monitored using Macbeth® Color-Eye 7000A which characterizes the color of an object in terms of L*, a*, and b*. Composition (2 mL each) was measured after dilution with 8 ml deionized water after 27 hours of stirring. The results for the Samples are presented below. The same indicate that ΔL* increased when adjuvant according to this invention was used.

| Sample | ΔL* |
| --- | --- |
| 1 (Control) | 52 |
| 2 | 62 |
| 3 | 68 |
| 4 | 80 |
| 5 | 85 | delta L* = color difference after stirring was completed versus initial.

Example 6

Compositions comprising KOjic acid or Allomaltol were made by mixing the following ingredients at room temperature. Mixing was achieved with moderate shear and the balance of the compositions made was water.

| Sample | DHA % | Glycine % | Kojic acid % | Allomaltol % |
| --- | --- | --- | --- | --- |
| 1 | 5 | 5 | 0.5 | — |
| 2 | 5 | 5 | 1 | — |
| 3 | 5 | 5 | 2 | — |
| 4 | 5 | 5 | 3 | — |
| 5 | 5 | 5 | — | 1 |
| 6 (Control) | 5 | 5 | — | — |

Visual observation and photographs after 6 hours of mixing at room temperature showed clear color development in the Samples. Samples 1 through 5 were shown to out perform the control by 93%, 130%, 203%, 256% and 193%, respectively, as determined by assessing the Samples with a spectrophotometer, wavelength 400 nm.

Visual observation and photographs were taken after 27 hours of mixing. Samples 1-5 were shown to out perform the control by 16%, 22%. 35%, 38% and 19%, respectively, as determined by assessing the Samples with a Spectrophotometer, wavelength 400 nm. These results illustrate the enhancement in tanning achieved with Kojic acid and Allomaltol.

Example 7

Compositions were made by mixing the following ingredients at room temperatures. Mixing was achieved with moderate shear and the balance of the compositions made was water. All percents are by weight.

| Sample | DHA % | Glycine % | Chlorinated Adjuvant* | Kojic acid |
|---|---|---|---|---|
| 1 (Control) | 5 | 5 | — | — |
| 2 | 5 | 5 | — | 0.25 |
| 3 | 5 | 5 | 0.25 | — |
| 4 | 5 | 5 | 0.5 | — |
| 5 | 5 | 5 | 1.5 | — |
| 6 | — | 5 | 0.25 | — |

*Kojic acid derivative with $CH_2Cl$ in lieu of $CH_2OH$.

The Samples were assessed for color development (with a Spectrophometer, 400 nm wavelength) three (3) days after mixing. The results revealed Samples 2 through 5 out-performed the control by 23%, 20%, 25% and 32%, respectively. No color body generation was observed when the chlorinated adjuvant was mixed with glycine and no DHA.

Example 8

The following compositions were mixed in a manner similar to the one described in Example 7.

| Sample | DHA % | Glycine % | Nitrogen comprising Allomatol derivative* (adjuvant) | Allomatol |
|---|---|---|---|---|
| 1 (Control) | 5 | 5 | — | — |
| 2 | 5 | 5 | — | 0.5 |
| 3 | 5 | 5 | 0.5 | — |
| 4 | 5 | 5 | 1 | — |
| 5 | 5 | 5 | 2 | — |
| 6 | — | 5 | 0.5 | — |

*Allomatol derivative with $NHCH_2COOH$ in lieu of OH.

The Samples were assessed (with a Spectrophotometer, 400 nm wavelength) fifteen (15) hours after mixing. The results revealed Samples 2 through 5 out performed the control by 40%, 17%, 2%, 6%, respectively. No color body generation was observed when the adjuvant was mixed with glycine and no DHA.

Example 9

Synthetic skin, VITRO-SKIN®, was purchased from IMS Inc. The same is conventionally known to mimic the surface properties of human skin.

About 6 mL solvent (Glycerin:$H_2O$=15:85 (w:w)) was used to dissolve material to make a total weight stock solution of 6 g and pH 5.7 was controlled with citric buffer. The substrate was cut into squares and treated with 20 microliters of the solution which was then spread smoothly within a 4.5 $cm^2$ circular area. The pieces of substrate were then stored in a desiccator containing an equimolar mixture of glycerol and water at 35° C. (50% relative humidity). Color developed on the synthetic skin substrate was monitored. The Compositions assessed are described below and were prepared by mixing all ingredients at ambient temperature under conditions of moderate shear. The balance of the compositions was water and all percents are by weight.

| Sample | DHA % | Glycine % | Allomatol % | Kojic acid % |
|---|---|---|---|---|
| 1 | 3 | — | — | — |
| 2 (Control) | 3 | 2.5 | — | — |
| 3 | 3 | 2.25 | 0.5 | — |
| 4 | 3 | 2.5 | 1 | — |
| 5 | 3 | 2.5 | 2 | — |
| 6 | 3 | 2.5 | — | 0.5 |
| 7 | 3 | 2.5 | — | 1 |
| 8 | 3 | 2.5 | — | 2 |

A colorimeter was used to obtain $\Delta L^*$ values for each Sample at 4, 22 and 51 hours.

| Sample | $\Delta L^{*i}$ |
|---|---|
| 1 | 3, 12, 14 |
| 2 | 17, 27, 26 |
| 3 | 21, 33, 32 |
| 4 | 22, 34, 36 |
| 5 | 23, 36, 37 |
| 6 | 22, 33, 35 |
| 7 | 21, 33, 34 |
| 8 | 23, 32, 38 |

$^i$= $\Delta L^*$ values at 4, 22 and 51 hours, read left to right.

The results demonstrate color enhancement was achieved on artificial skin.

What is claimed is:

1. A composition comprising:
   a) a sunless tanning agent comprising dihydroxyacetone; and
   b) an adjuvant for the sunless tanning agent comprising 3-hydroxy-6-methyl-4-pyrone or

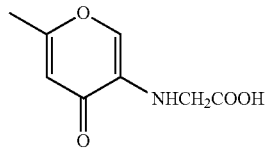

or a mixture thereof.

2. The composition according to claim 1 herein the composition further comprises a cosmetically acceptable carrier.

3. The composition according to claim 1 wherein the cosmetically acceptable carrier is an of emulsion.

4. The composition according to claim 1 wherein the composition further comprises a cationic ammonium compound.

5. The composition according to claim 4 wherein the cationic ammonium compound is 1,2-dihydroxypropyltrimonium chloride.

6. The composition according to claim 1 wherein the sunless tanning agent makes up from about 0.025 to about 35% by weight of the composition.

7. The composition according to claim 1 wherein the adjuvant makes up from about 0.025 to about 35% by weight of the composition.

8. The composition according to claim 1 wherein the composition has a pH from about 3 to about 4.75.

9. A method for imparting a sunless tan comprising the step of topically applying to skin the composition of claim 1.

* * * * *